United States Patent
Trapp et al.

(10) Patent No.: US 9,217,724 B2
(45) Date of Patent: Dec. 22, 2015

(54) POTENTIOMETRIC SENSOR AND METHOD FOR THE START-UP OF A POTENTIOMETRIC SENSOR

(75) Inventors: Thilo Trapp, Aliso Viejo, CA (US); Torsten Pechstein, Radebeul (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 172 days.

(21) Appl. No.: 13/324,057

(22) Filed: Dec. 13, 2011

(65) Prior Publication Data

US 2012/0152765 A1    Jun. 21, 2012

(30) Foreign Application Priority Data

Dec. 14, 2010  (DE) .......................... 10 2010 063 031

(51) Int. Cl.
| | |
|---|---|
| *G01N 27/26* | (2006.01) |
| *G01N 27/28* | (2006.01) |
| *G01N 27/403* | (2006.01) |
| *G01N 27/416* | (2006.01) |

(52) U.S. Cl.
CPC ........ *G01N 27/4035* (2013.01); *G01N 27/4163* (2013.01)

(58) Field of Classification Search
CPC ... G01N 27/26; G01N 27/28; G01N 27/4035; G01N 27/4163
USPC ....... 204/403.01–403.15, 411, 412, 204/414–416, 420; 205/787.5
See application file for complete search history.

(56) References Cited

U.S. PATENT DOCUMENTS

| | | | | |
|---|---|---|---|---|
| 4,413,628 A | * | 11/1983 | Tamulis | ......................... 600/361 |
| 6,016,201 A | | 1/2000 | Lin et al. | |
| 2002/0144905 A1 | * | 10/2002 | Schmidt | ................... 204/403.01 |
| 2006/0001431 A1 | | 1/2006 | Adami | |
| 2006/0027453 A1 | * | 2/2006 | Catalano et al. | .............. 204/435 |
| 2007/0185472 A1 | | 8/2007 | Baumfalk | |
| 2009/0139298 A1 | * | 6/2009 | Klees et al. | .................... 73/1.03 |

(Continued)

FOREIGN PATENT DOCUMENTS

| | | |
|---|---|---|
| DE | 4207845 C1 | 9/1993 |
| DE | 19539763 A1 | 4/1997 |

(Continued)

OTHER PUBLICATIONS

English Machine translation of DE 202005009297 U1.*

*Primary Examiner* — Susan D Leong
(74) *Attorney, Agent, or Firm* — Bacon & Thomas, PLLC (57) ABSTRACT

A potentiometric sensor includes a housing, in which a reference half cell space and a separated, measuring half cell space are formed. The reference half cell space contains a reference electrolyte and at least one part of a first potential sensing electrode for sensing a reference potential, and the measuring half cell space is liquid-tightly sealed by a measuring membrane, and contains an inner electrolyte and at least one part of a second potential sensing electrode for sensing a measuring half cell potential. A passageway extends through a wall of the housing, and opens into the reference half cell space, and is sealed relative to a medium surrounding the housing. The potentiometric sensor has a way for producing through the passageway an electrolytic contact between the reference electrolyte and the medium surrounding the housing.

16 Claims, 2 Drawing Sheets

(56) References Cited

U.S. PATENT DOCUMENTS

2010/0301060 A1   12/2010  Bernard
2011/0308947 A1*  12/2011  Wilke ........................... 204/414

FOREIGN PATENT DOCUMENTS

| | | |
|---|---|---|
| DE | 10123803 C1 | 10/2002 |
| DE | 202005009297 U1 * | 10/2005 |
| DE | 102005033727 A1 | 1/2007 |
| DE | 102006005533 A1 | 8/2007 |
| DE | 102008055107 A1 | 7/2010 |
| EP | 0520443 A2 | 12/1992 |
| EP | 1610120 B1 | 12/2005 |
| WO | WO 2010/072601 A1 | 7/2010 |
| WO | WO 2010072509 A1 * | 7/2010 |

* cited by examiner

POTENTIOMETRIC SENSOR AND METHOD FOR THE START-UP OF A POTENTIOMETRIC SENSOR

TECHNICAL FIELD

The invention relates to a potentiometric sensor, especially for application in single-use measurements technology for biological, pharmaceutical or biotech processes. The sensor comprises a housing, in which a reference half cell space and a therefrom separated, measuring half cell space are formed, wherein the reference half cell space contains a reference electrolyte and at least one part of a first potential sensing electrode for sensing a potential of the reference half-cell, and the measuring half cell space is sealed liquid-tightly by a measuring membrane, especially a pH-sensitive glass membrane, and has an internal electrolyte and at least one part of a second potential sensing electrode for sensing a potential of the measuring half cell.

BACKGROUND DISCUSSION

Pharmaceutical, chemical, biological, biochemical or biotech processes are, in increasing measure, performed in single-use containers (also referred to as disposables, or disposable bioreactors) as process containers. Such single-use containers can be, for example, flexible containers, e.g. bags, tubes or fermenters, or bioreactors. Bioreactors or fermenters frequently possess supply, and drain, lines, which can, for example, be embodied as tubes. In the supply, and drain, lines, also rigid tubular pieces can be inserted. After terminating a process, single-use containers can be disposed of. In this way, complex cleaning—and sterilization methods are avoided. Especially, through the use of single-use containers, the risk of cross contamination is prevented and, therewith, process safety is increased.

The processes performed in single-use containers proceed in a closed system, i.e. without connection to the environment outside the single-use containers. Since, frequently, sterile conditions are required, single-use container must be sterilized before introducing the process media. Frequently used for this purpose in biochemical, biological, biotechnological and pharmaceutical applications is gamma radiation. Also, in processes proceeding in a single-use fermenter or single-use reactor, the penetration of impurities, especially germs, from the environment into the interior of the process container must be prevented, in order not to degrade or corrupt the process flow.

In order to monitor or check the processes, it can be necessary to measure physical or chemical, measured variables of the media contained in the process container. Measured variables to be monitored can be, for example, temperature, pH-value, cell density, optical transmission or a concentration of a chemical substance, for example, a certain kind of ion, a certain element or a certain compound.

In published international patent application WO 2009/071829 A2 and German Offenlegungsschrift DE 10 2006 005 533 A1, complex mechanical coupling systems are described, which enable sterile introduction of an externally sterilized sensor into a single-use container.

Known from German Gebrauchsmuster DE 20 2007 000 152 U1 is an apparatus for securing an optical probe on a container having a flexible wall. In this case, the probe lies with a rear surface portion against an inner side of the container wall and extends with a central piece through an opening in the container wall, wherein the central piece is affixed by clamping to the container wall.

In order to configure the use of a container serving as a single-use fermenter or a single-use bioreactor especially simply, the potentiometric probe can be installed, already before the sterilization (to be effected, for example, by irradiation with gamma radiation), fixedly in a wall of the container and remain there for the duration of storage and use. While the actual use time of single-use containers amounts to only a few weeks, storage times can occur in the order of magnitude of one or more years.

Potentiometric sensors, for example, pH-glass electrodes or ion-selective electrodes, which are frequently embodied as single-rod, measuring chains, have a reference half cell and a measuring half cell, which contain a liquid or gel-like, inner electrolyte. The inner electrolyte of the reference half-cell, also referred to as the reference electrolyte, is in contact via a bridge, for example, a porous diaphragm, with the environment of the reference electrode, in order, in the measurement operation, in the case of immersion of the potentiometric sensor into a process medium to be monitored, to assure electrolytic contact between the reference electrolyte and the process medium. In this way, however, in the case of longer storage of a sensor in a single-use container, there is the danger that the reference electrolyte will dry out, or at least that air gets in via the bridge into the reference half cell space, such that the contact of the reference electrolyte with the environment is broken. Drying out can lead to drift and/or to decline of accuracy of measurement of the sensor. In the case of significant drying out of the reference electrolyte, the reference half-cell permanently stops working.

SUMMARY OF THE INVENTION

An object of the invention is to provide a potentiometric probe, which is suitable for monitoring a physical or chemical, measured variable of a measured medium to be monitored in a process container, especially also a flexible, process container, for example, a single-use fermenter or single-use bioreactor, especially also in its supply, or drain, lines, and which also assures still sufficient measurement quality in the case of long storage times.

The object is achieved by a potentiometric sensor comprising a housing, in which a reference half cell space and a therefrom separated, measuring half cell space are formed, wherein the reference half cell space contains a reference electrolyte and at least one part of a first potential sensing electrode immersed in the reference electrolyte for sensing a reference potential,
and the measuring half cell space is liquid-tightly sealed by a measuring membrane, especially a pH-sensitive glass membrane, and contains an inner electrolyte and at least one part of a second potential sensing electrode immersed in the inner electrolyte for sensing a measuring half cell potential, wherein a passageway extends through a wall of the housing, opens into the reference half cell space, and is, at least at times, sealed relative to a medium surrounding the housing, and wherein the potentiometric sensor has means for producing through the passageway an electrolytic contact between the reference electrolyte and medium surrounding the housing.

A reference half-cell of the potentiometric sensor is formed by the reference half cell space, the therein accommodated, reference electrolyte and the potential sensing electrode in the reference electrolyte. A measuring half cell of the potentiometric sensor is formed by the measuring half cell space, which therein accommodated, inner electrolyte and the therein immersed, sensing electrode.

The reference half-cell is at first, especially until start-up, completely sealed relative to the environment of the potentiometric sensor. For producing the electrolytic contact between the reference electrolyte and a medium, e.g. a process medium to be monitored, surrounding the housing required for measuring, the sensor includes means, to produce such a contact through the passageway between the reference half cell space and the environment. The terminology, electrolytic contact, means a connection between the reference electrolyte and the process medium at least effective for the exchange of charge carriers, especially ions, between the process medium and the reference electrolyte. Possible embodiments of this means are described below in yet greater detail. Since it is possible to produce electrolytic contact only when required, the sensor can be kept, for example, while in storage, i.e. before the first start-up for monitoring a biological, pharmaceutical or biotechnological process, completely sealed relative to the environment, in order to avoid a drying out of the inner electrolytes, especially the reference electrolyte, and to avoid therewith an associated compromising of the accuracy of measurement. Ideally, the electrolytic contact is produced first in the case of start-up. Thus, it is possible to store the inner electrolyte over a long period of time without compromising quality, so that after start-up a measuring of sufficient quality is assured.

The passageway can to this end be sealed at least at times with one or more closure means embodied to suppress, or at least to delay, the drying out of the reference half-cell. The terminology, drying out, means the evaporating and escape of liquid, especially a solvent, e.g. water, which forms a component of the reference electrolyte.

The passageway can be embodied, for example, in the form of a bore.

The potentiometric sensor can include a measurement circuit connected with the first and second potential sensing electrode and be embodied to register a potential difference between the reference potential and the measuring half cell potential and to output and/or to process such further as a measurement signal. The measurement circuit can especially have an analog/digital converter for digitizing the measurement signals. Moreover, the measurement circuit can have a plug contact for connecting the sensor with a superordinated unit, for example, with a conventional measurement transmitter, which can be connected with the plug contact via a cable connection.

The measurement circuit and the plug contact can be integrated in a plug head arranged on the end of the sensor lying opposite the measuring membrane. The plug head forms the housing for the measurement circuit and a mechanical and/or electrical interface for connecting a mechanical counterpart connected with the superordinated unit. The means for creating an electrolytic contact between the reference electrolyte and the process medium can be actuatable by connecting the plug head to the mechanical counterpart, for example, a cable connection. The mechanical counterpart can be, for example, a socket of a cable connection, into which the plug head of the sensor engages.

In an embodiment, the passageway can be sealed by means of an electrically conductive film, wherein the means for creating an electrolytic contact comprise electrical connections on the conductive film, via which the film is contactable with an electrical current pulse. By supplying the film with an electrical current pulse, the film can be destroyed, e.g. burned through or melted, so that a liquid passageway between the reference half cell space and the environment outside of the sensor housing arises through the passageway, and so that an electrolytic contact is produced between the reference electrolyte and a process medium, in which the sensor is immersed.

In another embodiment, the passageway is sealed with a wall, especially a membrane, a film or a plug, wherein the means for creating an electrolytic contact through the passageway comprise a pointed tool, especially a needle or a cannula, which is embodied, by a movement directed essentially axially relative to the passageway, to pierce through the wall or the plug, and so to produce a liquid passageway between the reference half cell space and the environment of the housing.

In another embodiment, there is guided through the passageway a push rod, which has a first section extending first within the reference half cell space and at least partially through the passageway and a second section protruding out from the passageway into the environment of the housing, wherein the diameter of the push rod in the first section is smaller than the inner diameter of the passageway and wherein the diameter of the push rod in the second section is larger than the inner diameter of the passageway. The transition between the first and the second section can be embodied as a radial shoulder, which in a first position before start-up of the sensor abuts outwardly on the housing wall and seals the passageway relative to the environment of the sensor housing. Before start-up, by an axial movement of the push rod relative to the passageway, the second section can be pushed further outwards, so that the shoulder is lifted off of the housing wall and an annular gap between the push rod and the passageway is formed, through which a liquid exchange between the reference half cell space and the environment becomes possible.

In an additional embodiment, the passageway can be sealed by a wall, a membrane, a film or a plug of a polymer material, which is insoluble in the reference electrolyte and dissolves ionic conductively and progressively in contact with a process medium, especially a feeding medium for microorganisms of a biotechnological process.

The reference electrolyte can be formed by a mixture of Ag/AgCl with a gel former. In such case, a hollow space within the reference half cell space can be filled partially with solid AgCl/KCl and the gel former, for example, cellulose, and be so embodied that, via an opening, later to be charged medium can penetrate, so that the KCl goes into solution. The potential sensing electrode of the reference half-cell is so arranged that it is in contact with the hollow space and the therein accommodated electrolyte.

A method for the start-up of a potentiometric sensor according to one of the previously described embodiments for monitoring a measured variable in a process includes steps as follows:
 providing the potentiometric sensor in a sealed process container;
 bringing an immersion region of the potentiometric sensor, which includes the measuring membrane and the passageway, in contact with a process medium of a desired process, especially a biotechnological process, in the process container; and
 producing an electrolytic contact between the reference electrolyte and the process medium.

The providing of the sensor in a sealed process container can occur, for example, by securing the sensor to connecting means provided in the process container wall, such that the sensor remains fixedly connected with the container wall. Another opportunity is to bond the sensor fixedly with the container wall and to integrate it into the wall, for example, by adhesion or welding. In such case, the sensor is preferably so secured in the container wall that at least one immersion region of the sensor provided for the contact with the process medium to be monitored protrudes into the container, while electrical connecting means of the sensor, via which the measurement circuit of the sensor can be connected with a superordinated electronics-unit, extend out of the container and/or are accessible from outside of the container.

The provided sensor in the process container can be sterilized simultaneously with the process container, for example, through irradiation with gamma radiation, and can be stored in the sterilized state for long periods of time, for example, over a period of time of more than a month, more than a year or even for a number of years.

The method can comprise performing a one-point calibrating of the potentiometric sensor based on a measured value of the potentiometric sensor registered in the process medium.

Especially, the one-point calibrating can comprise steps as follows:
registering, by means of the potentiometric sensor, a measured value of the measured variable of the process medium as current calibration measured value; and
updating a predetermined characteristic curve stored in a memory associated with the potentiometric sensor, especially in a superordinated unit connected with the potentiometric sensor, according to which characteristic curve a signal of the potentiometric sensor is mapped to a measured value, based on the current calibration measured value.

The term, calibrating, is frequently used, especially in pH-measuring, with a meaning other than generally usual. In general one means with 'calibrating' the reviewing of the display of a measuring device with a standard; the deviation between true value and display value is detected. The correcting of the display value to the true value is referred to as adjusting. Calibrating, in the case of the pH-sensor represents, strictly, an adjusting. Since the term calibrating is commonly used in electrochemistry, it is also used here.

The superordinated unit can be, for example, a data processing installation, for example, a measurement transmitter, which with the measurement circuit of the potentiometric sensor is connected. Via the connection, sensor signals are output to the data processing installation (on occasion via an intermediately connected, other circuit, which further processes and/or digitizes the sensor signals) and mapped in the data processing facility to a measured value based on a characteristic curve stored there. The characteristic curve can, in the case of a potentiometric pH-sensor or an ion-selective electrode, be a straight line, whose slope is predetermined, and whose zero-point, or axial crossing is fitted based on the one-point calibrating with application of the current calibration measured value. The fitting occurs based on a comparison of the current calibration measured value with the known value of the measured variable in the process medium. The value of the measured variable in the process medium can, for example, be known due to a reference measurement. Frequently in processes, however, also as regards certain measured variables, such as, for example, the pH-value, standardized process media are applied. Then the registering of a reference measured value can be omitted. Instead, the current calibration measured value can be compared with the measured value known due to the specification of the process medium.

The process medium can be a feeding medium for microorganisms of a biotechnological process and the chemical composition and its value of the measured variable to be monitored by the measuring device is known. In a biotechnological process, in which a desired product is produced by microorganisms, frequently, the organisms are supplied with a feeding medium, which must meet a strict specification. An important parameter of the feeding medium is, for example, the pH-value, which, as a rule, depending on the circumstances, must be accurate at least to a tolerance of 0.1 to 0.05 pH. On the basis of the known specifications of the feeding medium, thus, by comparison with the measured value registered by the sensor in the feeding medium, a one-point calibration can be performed, for example, in the previously described manner.

Besides pH-value, the measured variable to be monitored by the potentiometric sensor can also be an ion concentration of the measured medium.

The characteristic curve can be, for example, a straight line, wherein the zero-point (axial intercept) of the line is corrected based on the current calibration measured value.

The process container can be a single-use container for application in a biotechnological process, especially a flexible container, a bag-fermenter, a hose, or a tubular connection.

BRIEF DESCRIPTION OF THE DRAWINGS

The invention will now be explained in greater detail based on the examples of embodiments illustrated in the drawing, the figures of which show as follows.

DETAILED DISCUSSION IN CONJUNCTION WITH THE DRAWINGS

Figure 1:
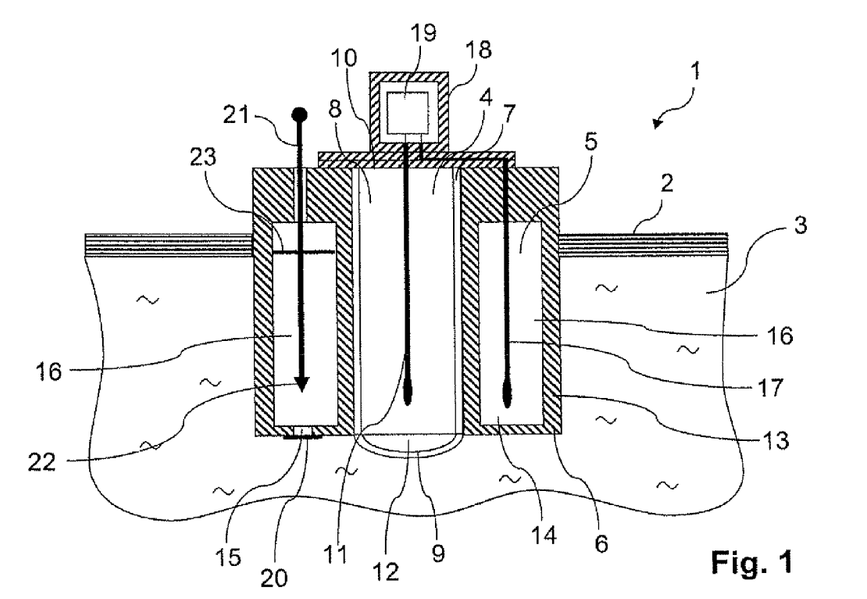
FIG. 1 is a schematic representation of a potentiometric sensor in a first embodiment before start-up.

FIG. 1 shows schematically, as first example of an embodiment, a potentiometric pH-sensor 1, which is affixed in the wall of a flexible, single-use container 2. Contained in single-use container 2 is a process medium 3, in the present example a feeding medium for microorganisms of a biotechnological process. Sensor 1 can be welded in in the wall of single-use container 2, or also be affixed mechanically releasably in a connector. Sensor 1 includes a measuring half cell 4 and a reference half cell 5, which are formed in a housing 6 of a non electrically conductive material, for example, glass and/or synthetic material, such as a plastic.

Measuring half cell 4 comprises an inner, tubular, housing part 7, which surrounds a measuring half cell space 8. Measuring half cell space 8 is sealed on its media-side end by a pH-sensitive, measuring membrane 9 and has on its oppositely lying end 10 a closure (not illustrated in greater detail), through which a potential sensing electrode 11 is led, which serves for sensing the measuring half cell potential. Sensing electrode 11 can be, for example, a metal wire, for example, a silver wire. The closure can be formed by an adhered joint, a melted joint of the housing wall or a plug or stopper. Measuring half cell space 8 is at least partially filled with an inner electrolyte 12, preferably a buffer solution, in which the potential sensing electrode 11 is immersed. Electrode 11 serves for sensing the potential arising at the measuring membrane 9, which is a measure for the H+−, or $H_3O+$ ion content of the process medium 3, i.e. a measure for the pH-value of the process medium 3.

Reference half cell 5 includes a reference half cell space 14 surrounded by an outer, housing part 13 forming an annular chamber. The annular housing part 13 surrounds the tubular housing part 7 containing the measuring half cell 4 and is connected with such fixedly, so that the reference half cell 5 and measuring half cell 4 together form a single-rod measuring chain. In a media-side immersion region of the potentiometric sensor 1 provided for contact with the process medium 3, the annular chamber shaped, housing part 13 has a passageway 15, which extends from the reference half cell space 14 through a, here, media-side, wall of the housing part 13 out to the environment, and so forms a connection between the reference half cell space 14 formed in the housing part 13 and the environment of the sensor 1, thus the interior of the process container 2. Reference half cell space 14 is at least partially filled with a reference electrolyte 16, in which is immersed a potential sensing electrode 17 embodied as a chloridized silver wire. Serving as reference electrolyte 16 can be, for example, an aqueous 3 M KCl solution.

Arranged on the end of the potentiometric sensor facing away from the medium and protruding out from single-use container 2 is a plug head 18. Plug head 18 surrounds and protects a therein accommodated, measurement circuit 19, which is connected conductively with the potential sensing electrode 11 of the measuring half cell and the potential sensing electrode 17 of the reference half cell, and which is embodied to register a potential difference between the measuring half cell 4 and the reference half cell 5 and to output such as a measurement signal. Optionally, the measurement circuit 19 can have an analog/digital converter for digitizing the measurement signal. Plug head 18 forms an interface for connecting a connection counterpiece, for example, a cable, which connects the sensor 1 with a superordinated unit, for example, a measurement transmitter, in order to forward the measurement signal to the superordinated unit, which further processes the measurement signal.

Passageway 15 is sealed in the state before start-up of the sensor 1, as shown in FIG. 1, by a membrane 20. for example, a polymer membrane, which is applied on the outside of the housing part 13 and completely covers the passageway 15. Alternatively, the passageway 15 can also be sealed by a metal foil or a plug or stopper. An option is also to provide, instead of a passageway 15, a blind bore, which so protrudes deeply into the housing wall inwardly that, on the reference half cell side or on the outside, only a thin, membrane-like housing wall remainder is left, which seals the bore relative to the environment of the housing part 13. The oppositely lying housing wall of the housing part 13 includes another passageway, through which a push rod 21 is axially led, which has on its end facing the membrane 20 a pointed tool 22, for example, a needle or a cannula. On its end protruding out from the housing part 13, opposite the pointed tool 22, the push rod has a thickening, which serves as a stop for an axial movement of the push rod in the direction the membrane 20. The push rod 21 is fixedly connected with a return element 23 arranged within the reference half cell space 14 and, affixed to the housing wall of the housing part 13. In the example shown here, the return element is embodied as an elastic barrier. In the resting position of the push rod 21 illustrated in FIG. 1, such is held by the return element 23 in an axial position, in which the pointed tool 22 is retracted into the reference half cell space 14. Preferably, the reference half cell space 14 is sealed relative to the environment of the process container 2, for example, by a sealing element (not shown) arranged in the annular gap between the push rod 21 and the additional passageway, in order to assure the sterility of the container interiors.

Figure 2:
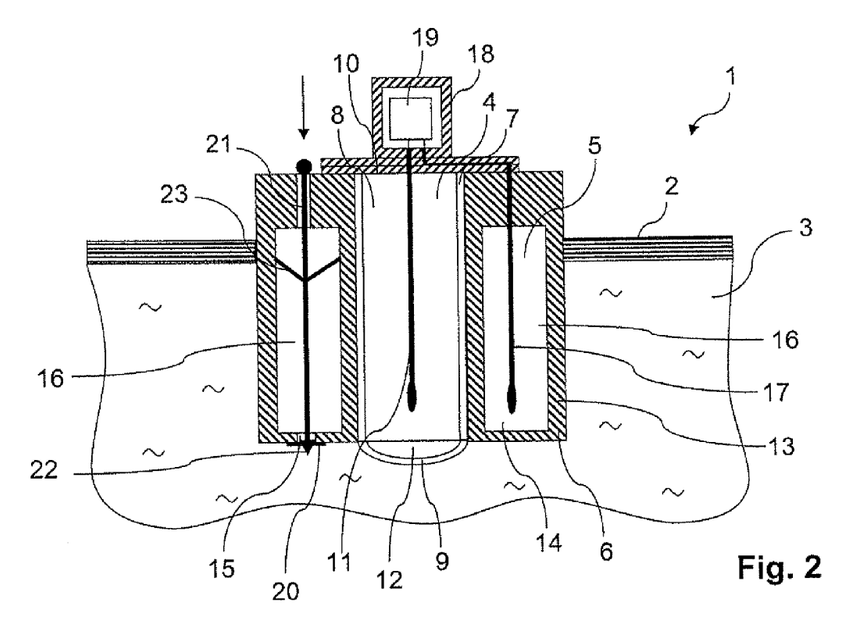
FIG. 2 is a schematic representation of the potentiometric sensor in the first embodiment after start-up.

FIG. 2 shows schematically the start-up of the potentiometric sensor 1 of the first example of an embodiment. For this, there occurs, through exertion of force in the arrow direction on the push rod 21, an axial movement of the push rod 21 toward the membrane 20, so that the pointed tool 22 is inserted into the passageway 15 and pierces the membrane 20. The membrane 20 and, correspondingly, also an alternatively applied film, wall plug or stopper, is therefore embodied so thinly that it can be pierced by exertion of force on the push rod. By way of the return force exerted by the return element 23 on the push rod 20, the push rod 21 is moved back into its resting position. The pierced membrane 20 then permits liquid exchange, especially exchange of charge carriers, between the reference half cell space 14 and the environment of the housing 6. Thus, an electrolytic contact is produced between the reference electrolyte 16 and the process medium surrounding the sensor 1 at least in its immersion region 3.

Figure 3:
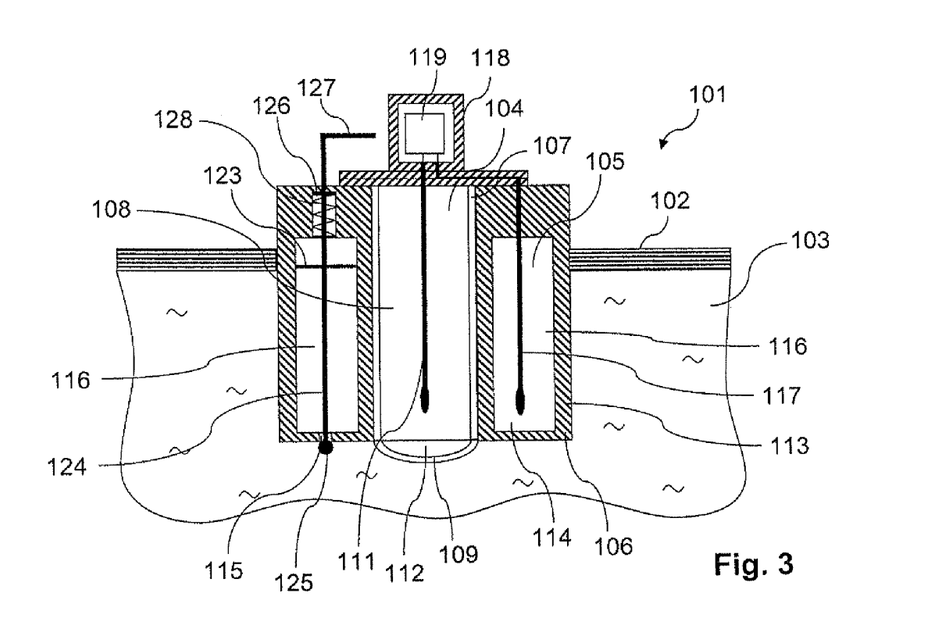
FIG. 3 is a schematic representation of the potentiometric sensor in a second embodiment before start-up.

FIG. 3 shows, as second example of an embodiment, a potentiometric pH-sensor 101, which is likewise integrated fixedly into the wall of a single-use container 102 containing a process medium 103. The construction of sensor 101 is, as regards the embodiment of the measuring half cell 104 and the reference half cell 105 essentially identical with the construction of the sensor 1 described in the first example of an embodiment. Measuring half cell 104 includes likewise a tubular housing part 107 surrounding a measuring half cell space 108. Measuring half cell space 108 is sealed on its media-side end by a pH-sensitive, measuring membrane 109, for example, a glass membrane, and on its rear-side end by a closure, through which a potential sensing electrode 111 is led. Located in the measuring half cell space 108 is an inner electrolyte 112, into which the potential sensing electrode 111 protrudes for sensing the membrane potential dependent on the pH-value. Reference half cell 105 includes, same as the reference half cell 5 of the first example of an embodiment, a housing part 113 forming an annular reference half cell space 114. Housing part 113 is fixedly connected with the housing part 107 of the measuring half cell 108 for forming a single-rod measuring chain. Reference half cell space 114 is filled at least partially with a reference electrolyte 116, for example, a 3 M KCl solution, in which a potential sensing electrode 117 embodied as a chloridized silver wire is immersed. Arranged on the end of sensor 101 protruding out from the single-use container 102 is a plug head 118, in which a measurement circuit 119 connected with the potential sensing electrodes 111, 117 is accommodated. Plug head 118 serves as in the first example of an embodiment as an interface for connection with a superordinated unit, e.g. a measurement transmitter, to which the measurement signals of the measurement circuit 119 produced and output based on the potential difference registered between the sensing electrodes 111, 117 can be forwarded for additional processing.

The medium-side wall of the housing part 113 includes, communicating with the reference half cell space 114, a passageway 115, through which a push rod 124 is led. The push rod 124 has, arranged within the reference half cell space 114 and extending through the passageway 115, a first section, whose diameter is smaller than the diameter of the passageway 115. Adjoining this first section and protruding out from the passageway 115 is a second section, which is embodied as a thickening 125 of the push rod 124 and having a diameter, which is larger than the diameter of the passageway 115. The transition between the first and the second sections forms a stop 125 abutting externally against the wall of the housing part 113.

Push rod 124 extends through another passageway 126 in the oppositely lying wall of the housing part 113 and protrudes from this out into the sensor environment. The annular gap between the push rod 124 and the passageway 126 is sealed relative to the environment of the container 102, in order, on the one hand, to assure the state of sealing of the reference half cell space 114 during storage of the sensor 1 and, on the other hand, to assure the sterility of the process container 102 during the process. Secured on the end of push rod 124 is a driving pin 127 extending perpendicular thereto. Arranged in a section of the additional passageway 126 is a spring 128, which is fixedly connected on one end with the push rod 124 or lies against a radial shoulder or one or a number of radially arranged noses of the push rod 124 and on its other end is supported against a shoulder embodied as a narrowing of the additional passageway 126.

In the state of sensor 101 before start-up as illustrated in FIG. 3, the spring 128 is biased against this shoulder, so that the stop 125 lies securely against the outside of the housing part 113. In this state, the reference half cell space 114 is sealed completely relative to the environment, especially relative to the process medium 103.

Figure 4:
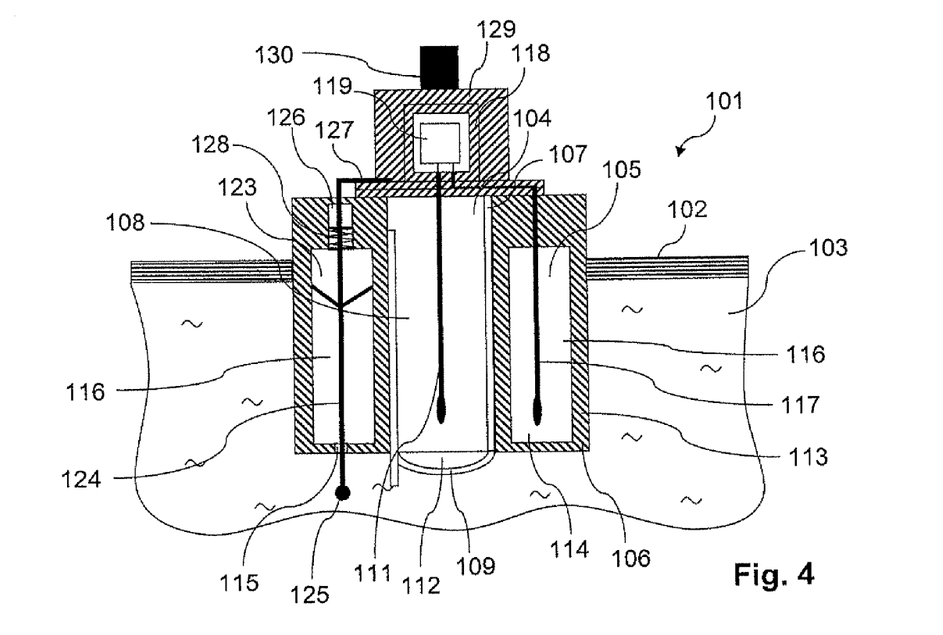
FIG. 4 is a schematic representation of the potentiometric sensor in the second embodiment after start-up.

If, as shown in FIG. 4, in the case of start-up of sensor 101, the plug head 118 is connected with a counterpart 129, for example, a socket of a connection cable 130 of a superordinated unit, the driving pin 127 is moved by the counterpart 129 in the media-side direction, so that an axial shifting of the push rod 124 in the media-side direction is effected. For this, a guide interacting with the driving pin 127 can be provided in the counterpart 129. In such case, the spring 128 is more strongly pressed against the shoulder provided in the additional passageway 126. At the same time, the push rod 124 is pushed further into the process medium 103, so that the stop 125 is lifted off of the passageway 115 and an annular duct is opened between the push rod 124 and the inner wall the passageway 115. Through the annular duct, an exchange of liquid and especially charge carriers becomes possible, so that an electrolytic contact is produced between the reference electrolyte 116 and the process medium 103. If the counterpart 129 is removed from the plug head 118, the return force of the spring 128 effects a drawing back of the push rod 124 and, associated therewith, the renewed closing of the passageway 115 by the stop 125.

In the case of both examples of embodiments described here and in the case of the above described, additional possible embodiments of the sensor, upon start-up, after producing an electrolytic connection between the reference electrolyte and the process medium, a one-point calibrating can be performed.

A method for start-up of the sensor according to one of the two examples of embodiments previously described at length or according to one of the above described, additional embodiments will now be described in detail.

The sensor is first provided in a process container, especially a single-use process container. For this, it is, for example, affixed in a connector of the process container provided therefor or connected fixedly with the process container wall, for example, by welding or adhesive. In such case, a part of the sensor, including the immersion region provided for contact with the process medium later to be monitored, protrudes into the interior of the process container. The immersion region includes at least the sensitive, measuring membrane and the before start-up, still sealed passageway, via which, later, the electrolytic contact between the reference electrolyte and the process medium is produced. Another, rear part of the sensor, which includes at least the plug head and a rear-side section of the push rod, is located outside of the single-use container or at least is accessible outside of the single-use container.

After providing the sensor in the single-use container, this can be subjected with the sensor to a sterilization, for example, by irradiation with gamma-radiation. Thereafter, the sterilized container is stored until it is needed for performing a process. Since the electrolyte containing, reference half cell space is sealed completely relative to the environment, a drying out of the electrolyte and, associated therewith, a worsening of the measurement quality, or a completely worthless sensor, are avoided.

When the single-use container is finally needed for performing a method, for example a biotechnological method, the sensor is made ready for operation. For this, as previously described in different ways, a connection is produced between the reference half cell space and the interior of the process container, via which an exchange of charge carriers, especially ions, can occur. Additionally, a superordinated unit, for example, a measurement transmitter, is connected to the sensor plug head. The superordinated unit possesses an evaluation circuit for processing the measurement signals obtained by the sensor. The evaluation circuit is embodied, in manner known per se, to associate with a measurement signal of the sensor a measured value of the measured variable to be monitored by the sensor based on a characteristic curve stored in its memory. If the sensor is a potentiometric pH-sensor, the characteristic curve is, as a rule, a straight line, which is described by its zero-point, or abscissa intercept, and a slope.

Fed to the process container is, first, a first process medium. Preferably, the first process medium is a substance, which has a known value of the measured variable to be monitored by the sensor. The following explanations relate to monitoring the pH-value, but they hold, however, in equal manner, for monitoring other measured variables. The pH-value of the first process medium can, for example, have been ascertained by an earlier performed, reference measurement. Frequently, also process media are applied, which are subject to a strict specification. This is true, for example, for feeding solutions in biotechnological processes. The feeding solutions are exactly specified as regards its pH-value to tolerances of 0.1 to 0.05 pH. When an electrolytic connection between the reference electrolyte of the sensor and the first process medium is produced, the first process medium, for example, the feeding solution, can be utilized for performing a one-point calibrating of the sensor.

For performing the one-point calibrating, the pH-value of the process medium, for example, the feeding solution, is registered with the sensor and mapped to a measured value. On the basis of the comparison between the known actual pH-value of the feeding medium and that based on the sensor signal, the characteristic curve is fitted. In the present case a lines is thus fitted to the zero-point, or the abscissa intercept. Alternatively, it is also possible to compare the measurement signal of the pH-sensor with a theoretical signal calculated from the known pH-value of the process medium, for example, based on the Nernst-equation, and based on this comparison, to adjust the zero-point, or the abscissa intercept, of the characteristic curve.

In the case of little chemically, mechanically or thermally burdened pH-sensors, the slope is in the region of 58-59 mV/pH, near the theoretical value of 59.2 mV/pH, at 25° C. Since the zero-point of the described pH-sensors with a pH-sensitive glass membrane lies, as a rule, at pH-7, errors from an insufficiently calibrated slope first become significant at pH-values differing strongly from pH=7. An error from an insufficiently calibrated zero-point acts, in contrast, over the total pH measuring range. Since especially in biotechnological processes, in which microorganisms are used, as a rule, the pH-value is kept in the range of pH=6 to 8, an insufficiently calibrated zero-point is here the main error. A one-point calibration in the here described manner is therefore sufficient in such applications, in order to eliminate the main errors degrading the accuracy of measurement.

After the one-point calibrating is done, other process media, especially in one of the described biotechnological applications, the required microorganisms, can be introduced into the single-use container.

The invention claimed is:

1. A potentiometric sensor comprising:
    a housing, in which a reference half cell space and a separated, measuring half cell space are formed, wherein said reference half cell space contains a reference electrolyte and at least one part of a first potential sensing electrode immersed in the reference electrolyte for sensing a reference potential, and said measuring half cell space is liquid-tightly sealed by a measuring membrane, and contains an inner electrolyte and at least one part of a second potential sensing electrode immersed in the inner electrolyte for sensing a measuring half cell potential;
    a passageway which extends through a wall of said housing, opens into said reference half cell space, and is sealed relative to a medium surrounding said housing; and
    means for producing through said passageway an electrolytic contact between said reference electrolyte and medium surrounding said housing, wherein:
    said passageway is sealed by a wall, film or membrane or a plug or stopper of a polymer materials, which is insoluble in the reference electrolyte, and, in contact with a process medium which progressively dissolves the seal.

2. The potentiometric sensor as claimed in claim 1, further comprising:
    a measurement circuit, which is connected with said first and said second potential sensing electrode, and which is embodied to register a potential difference between the reference potential and the measuring half cell potential and to output said registered potential difference as a measurement signal and/or to process said registered potential difference further.

3. The potentiometric sensor as claimed in claim 1, wherein:
    said reference electrolyte is formed by a mixture of Ag/AgCl-cellulose.

4. The potentiometric sensor as claimed in claim 1, wherein:
    said measuring membrane is a pH-sensitive glass membrane.

5. The potentiometric sensor as claimed in claim 2, wherein:
    said measurement circuit is accommodated in a plug head arranged on an end of the potentiometric sensor facing away from said measuring membrane.

6. The potentiometric sensor as claimed in claim 5, wherein:
    said first potential sensing electrode and said second potential electrode both comprising a silver wire.

7. A sensor arrangement comprising:
    a single-use container containing a process medium and a potentiometric sensor affixed in a wall of said single-use container, said potentiometric sensor comprising:
    a housing, in which a reference half cell space and a separated, measuring half cell space are formed, wherein said reference half cell space contains a reference electrolyte and at least one part of a first potential sensing electrode immersed in the reference electrolyte for sensing a reference potential, and said measuring half cell space is liquid-tightly sealed by a measuring membrane, and contains an inner electrolyte and at least one part of a second potential sensing electrode immersed in the inner electrolyte for sensing a measuring half cell potential; and
    a passageway which extends through a wall of said housing, opens into said reference half cell space, and is sealed relative to the process medium surrounding said housing;
    said passageway is sealed with a wall or a plug or stopper; and
    said sensor further comprises:
    a pointed tool which is embodied, by a movement directed essentially axially relative to said passageway, to pierce through said wall or said plug or said stopper, and so to produce a liquid passageway between said reference half cell space and the process medium, wherein:
    the pointed tool is connected to a push rod, said push rod is axially led through another passageway in a housing wall lying oppositely with respect to the wall through which said passageway extends.

8. The sensor arrangement as claimed in claim 7, wherein:
    said pointed tool is a needle or a cannula.

9. A potentiometric sensor comprising:
    a housing, in which a reference half cell space and a separated, measuring half cell space are formed, wherein said reference half cell space contains a reference electrolyte and at least one part of a first potential sensing electrode immersed in the reference electrolyte for sensing a reference potential, and said measuring half cell space is liquid-tightly sealed by a measuring membrane, and contains an inner electrolyte and at least one part of a second potential sensing electrode immersed in the inner electrolyte for sensing a measuring half cell potential;
    a passageway which extends through a wall of said housing, opens into said reference half cell space, and is sealed relative to a medium surrounding said housing;
    there is led through said passageway a push rod, which has a first section extending first within said reference half cell space and at least partially through said passageway and a second section protruding out from said passageway into the environment of said housing;
    the diameter of said push rod in the first section is smaller than the inner diameter of said passageway; and
    the diameter of said push rod in the second section is larger than the inner diameter of said passageway.

10. A potentiometric sensor comprising:
    a housing, in which a reference half cell space and a separated, measuring half cell space are formed, wherein said reference half cell space contains a reference electrolyte and at least one part of a first potential sensing electrode immersed in the reference electrolyte for sensing a reference potential, and said measuring half cell space is liquid-tightly sealed by a measuring membrane, and contains an inner electrolyte and at least one part of a sensing potential sensing electrode immersed in the inner electrolyte for sensing a measuring half cell potential;
    a passageway which extends through a wall of said housing, opens into said reference half cell space, and is sealed relative to a medium surrounding said housing; and means for producing through said passageway an electrolytic contact between said reference electrolyte and medium surrounding said housing, wherein:
said passageway is sealed by a wall, film or membrane or a plug or stopper of a polymer material, which is insoluble in the reference electrolyte, and, in contact with a feeding medium for microorganisms of a biotechnological process which progressively dissolves the seal.

11. The potentiometric sensor as claimed in claim 7, further comprising:
a measuring circuit, which is connected with said first and second potential sensing electrode, and which is embodied to register a potential difference between the reference potential and the measuring half cell potential and to output said registered potential difference as a measurement signal and/or to process said registered potential difference further.

12. The potentiometric sensor as claimed in claim 11, wherein:
said measurement circuit is accommodated in a plug head arranged on the end of the potentiometric sensor lying opposite said measuring membrane; and
the pointed tool is actuable by connecting said plug head to a connector connected with a superoperordinated unit.

13. The potentiometric sensor as claimed in claim 7, wherein:
said reference electrolyte is formed by a mixture of Ag/AgCl-cellulose.

14. The potentiometric sensor as claimed in claim 9, further comprising:
a measurement circuit, which is connected with said first and second potential sensing electrode, and which is embodied to register a potential difference between the reference potential and the measuring half cell potential and to output said registered potential difference as a measurement signal and/or to process said registered potential difference further.

15. The potentiometric sensor as claimed in claim 14, wherein:
said measurement circuit is accommodated in a plug head arranged on the end of the potentiometric sensor lying opposite said measuring membrane; and
the push rod is actuable by connecting said plug head to a container connected with a superoperordinated unit.

16. The potentiometric sensor as claimed in claim 9, wherein:
said reference electrolyte is formed by a mixture of Ag/AgCl-cellulose.

* * * * *